United States Patent
Springs

[19]

[11] Patent Number: 5,865,776
[45] Date of Patent: Feb. 2, 1999

[54] KNEE BRACE HAVING DIFFERENTIAL FLEXIBILITY POSTERIOR AND ANTERIOR PANELS

[75] Inventor: Michael A. Springs, Leawood, Kans.

[73] Assignee: Ortho-Care, Inc., Raytown, Mo.

[21] Appl. No.: 838,639

[22] Filed: Apr. 9, 1997

[51] Int. Cl.[6] .................................................. A61F 5/00
[52] U.S. Cl. ............................................. 602/26; 602/63
[58] Field of Search ................... 602/5, 12, 23, 602/26, 61–63; 128/DIG. 15

[56] References Cited

U.S. PATENT DOCUMENTS

| | | | |
|---|---|---|---|
| 3,945,046 | 3/1976 | Stromgren | 602/63 |
| 4,116,236 | 9/1978 | Albert | 602/26 |
| 4,287,885 | 9/1981 | Applegate | 602/26 |
| 4,296,744 | 10/1981 | Palumbo | 602/63 X |
| 4,870,956 | 10/1989 | Fatool et al. | 602/63 X |
| 4,941,462 | 7/1990 | Lindberg | 602/26 X |
| 5,024,216 | 6/1991 | Shiono | 602/26 |
| 5,139,477 | 8/1992 | Peters | 602/26 |
| 5,154,690 | 10/1992 | Shiono | 602/63 X |
| 5,263,923 | 11/1993 | Fujimoto | 602/63 X |
| 5,277,697 | 1/1994 | France et al. | 602/26 X |
| 5,382,223 | 1/1995 | Springs . | |
| 5,399,153 | 3/1995 | Caprio Jr. et al. | 602/63 X |
| 5,462,517 | 10/1995 | Mann | 602/26 |

FOREIGN PATENT DOCUMENTS

| | | | |
|---|---|---|---|
| 2606998 | 5/1988 | France | 602/63 X |
| 3028381 | 2/1982 | Germany | 602/63 |
| 3416231 | 11/1985 | Germany | 602/63 |
| 91/01704 | 2/1991 | WIPO | 602/63 |

OTHER PUBLICATIONS

Darlexx Performance Characteristics Information Sheet.

*Primary Examiner*—Linda C.M. Dvorak
*Attorney, Agent, or Firm*—Hovey, Williams, Timmons & Collins

[57] ABSTRACT

An improved knee-supporting sleeve (10) is provided having posterior and proximal anterior panels (12, 20) formed of thin relatively highly stretchable material, with a distal anterior panel (22) formed of less stretchable composite materials. The sleeve (10) thus provides maximum-support and joint conformity, together with good breathability and thermal properties. The sleeve (10) also has a patella-receiving opening (42) and an adjacent buttress (52) housed within a selectively openable compartment (44) to trim and/or shift buttress (52) therein, so that a desirable "lateral J" buttress may be provided for either a left or right knee.

20 Claims, 3 Drawing Sheets

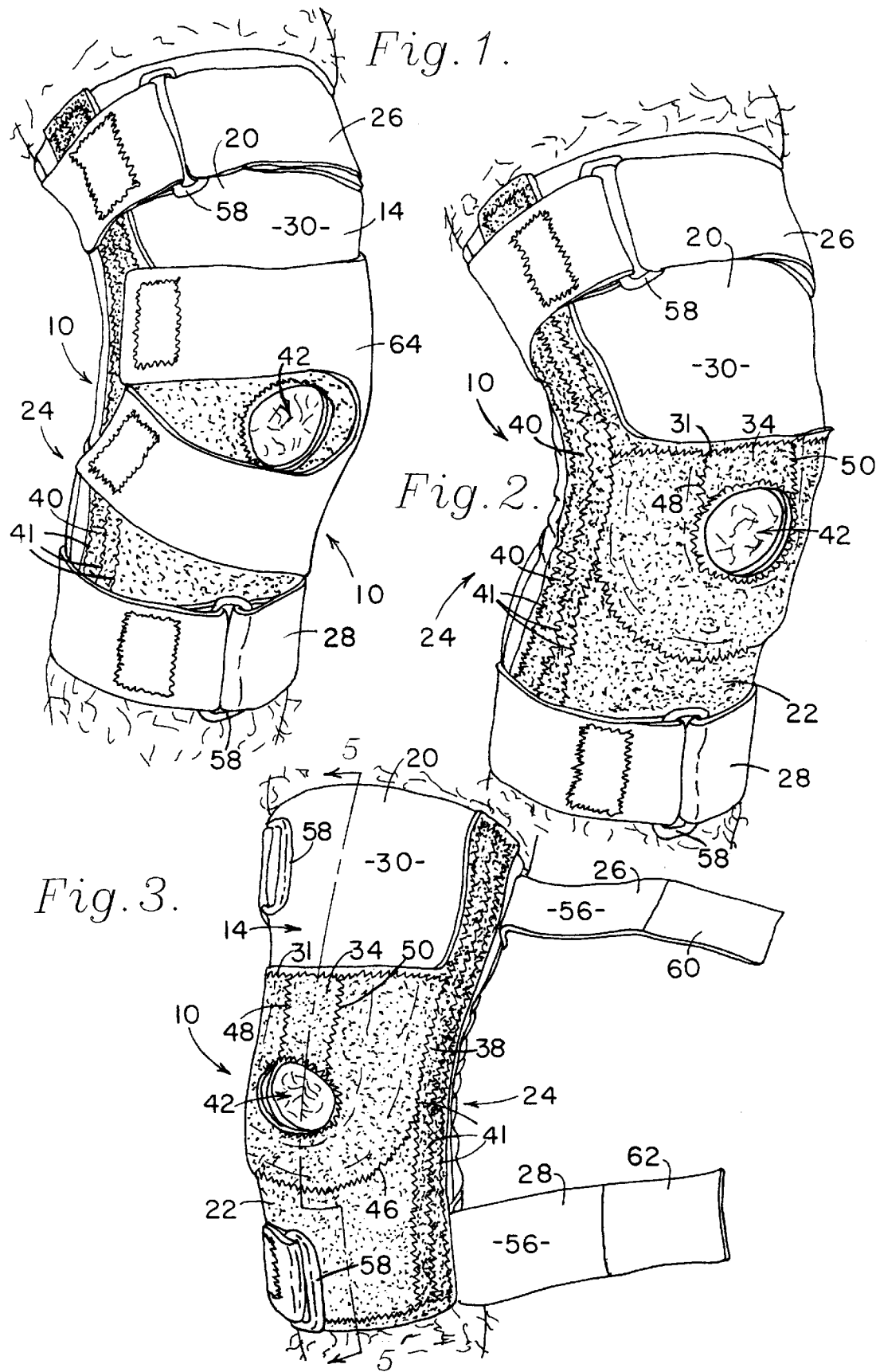

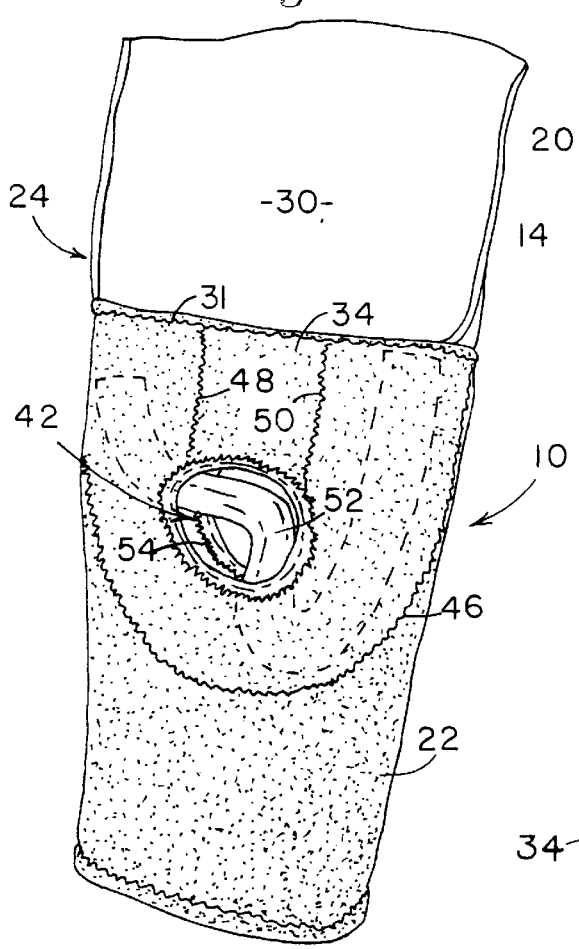
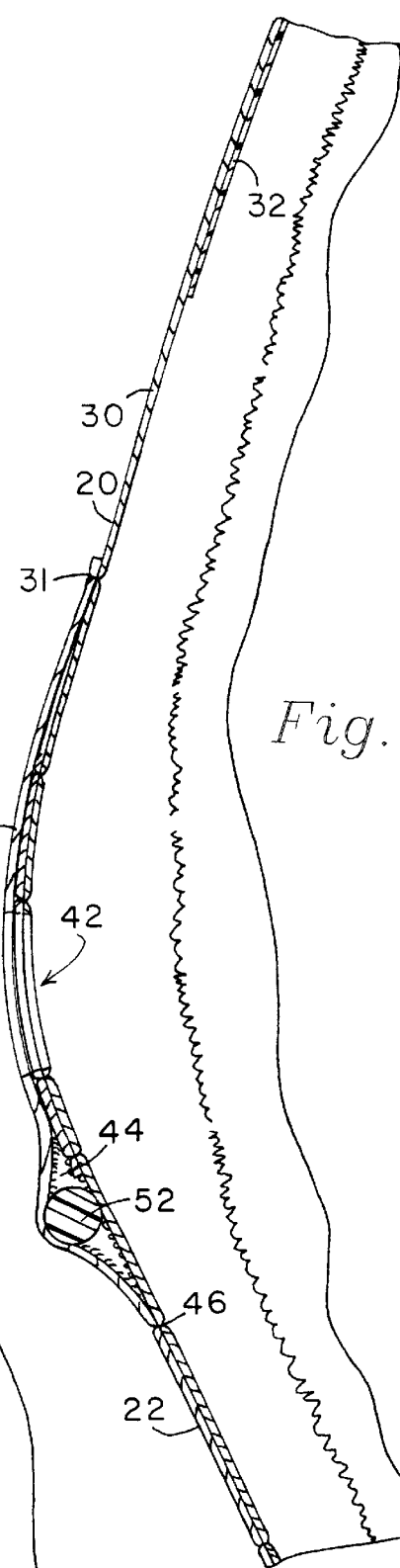
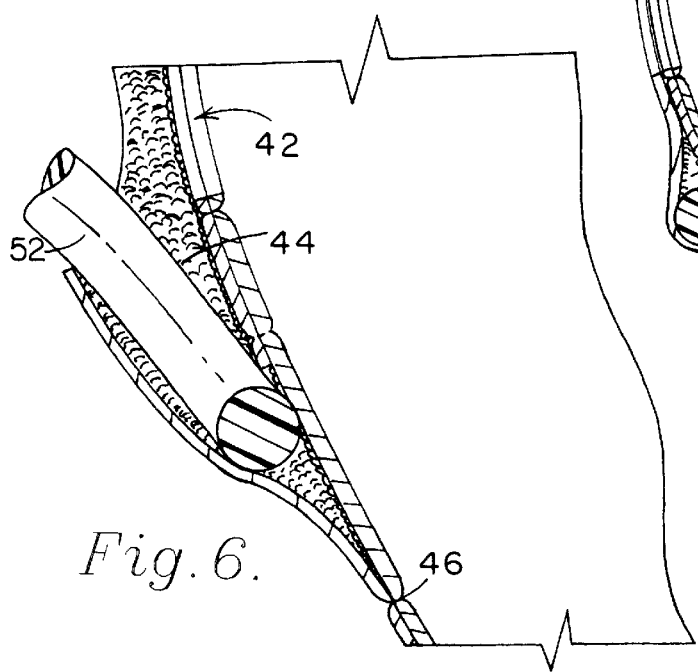

KNEE BRACE HAVING DIFFERENTIAL FLEXIBILITY POSTERIOR AND ANTERIOR PANELS

BACKGROUND OF THE INVENTION

1. Field of the Invention

The present invention is broadly concerned with knee-supporting orthopaedic sleeve supports having posterior and anterior panels giving differential stretch characteristics so as to provide a unique combination of compression, knee area conformity and support, while also giving optimum thermal and evaporation properties. More particularly, the invention pertains to such knee sleeves which preferably have highly stretchable posterior and proximal anterior panels formed of a thin, lightweight, three-ply laminate, with a distal anterior panel formed by securing a faced, VELCRO-compatible neoprene material to the inner lightweight laminate. In further preferred forms, the sleeves of the invention are provided with a patella-receiving opening in the anterior panel thereof, together with an adjustable knee buttress. The latter is housed within an openable compartment on the outer face of the anterior panel to allow access to the buttress therein to permit trimming and/or adjustment of the buttress. In this fashion, the buttress can be selectively trimmed and positioned by the user as a "lateral J" buttress for either the right or left knee.

2. Description of the Prior Art

Tubular orthopaedic supports have long been produced for use by individuals to support weak or injured limbs during rehabilitation or as a general protective measure. Very commonly, tubular knee supports are used by athletes and generally include an elongated, tubular body adapted to be placed over the knee, lower thigh and upper calf regions of the leg. Many such knee supports include padding, lateral bracing and external straps for proper positioning and maximum comfort and support. Modern-day orthopaedic knee sleeves of this type are often fabricated using closed cell neoprene rubber sleeves, which may be lined with a soft terry or nylon fabric.

Orthopaedic knee supports can be in the form of simple tubular or frustoconical, open-ended bodies. These units are considered rather crude, however, and suffer from the problems of gathering at the knee and falling during exercise. It has also been known in the past to provide anatomically contoured supports which are designed to more closely conform with the knee area. These units generally include an outwardly flaring upper section designed to receive the lower thigh, a recessed central region, and a lower, diverging, calf-receiving section. Contoured supports of this type are generally preferred, in that they avoid many of the problems of simple tubular designs.

U.S. Pat. No. 5,382,223 describes anatomically contoured knee supports which are specially designed to be free of posterior, transverse dart-defining seams, thereby avoiding abrasion and irritation to the popliteal region of the knee joint during walking or exercise. Accordingly, the '223 patent represents a distinct advance in the art.

U.S. Pat. No. 4,492,227 discloses an elastic knee bandage formed of three distinct, interconnected tubular sections. The central knee-engaging section of the bandage is designed to have from 2–10 times the elastic stretch of the adjacent upper and lower sections of the bandage. Thus, the '227 patent teaches that the greatest degree of flexibility in the knee bandage be at the area of the knee proper, whereas stiffer and less stretchable segments are provided above and below the knee.

U.S. Pat. No. 4,084,584 describes a knee sleeve having a central, anterior patella-receiving opening therethrough. In addition, this patent teaches the use of a stationary, semi-circular knee buttress positioned on the outside of the leg in order to restrict lateral outward movement of the knee cap. More recent manifestations of this concept have involved the use of "lateral J" knee buttresses which are positioned adjacent the patella-receiving opening with the upright portion of the "J" along the outer edge of the patella and the lower curved portion of the "J" beneath the patella. The use of such knee buttresses has required manufacturers to make right and left handed versions of the knee supports, i.e., the "J" buttress is positioned oppositely for right and left knees. This not only increases manufacturing costs, but also requires the distributor and seller to stock handed versions of the supports.

Additional patents describing various knee and orthopaedic supports, and materials used therein, include U.S. Pat. Nos. 4,320,634, 3,613,681, 4,446,181, 5, 085,210, 4,388,134, 4,908,037, 4,832,010, 4,961,418, 4,790,855, and 4,822,371. Other disclosures are found in UK Patent Application 2,111,833 and Italian Patent No. 684,333.

Thus, while there has been significant design activity in the field of orthopaedic knee supports, there remains an unfulfilled need for a knee supporting sleeve which provides optimum compression and support, knee joint conformity and thermal properties. At the same time, it would be a distinct advance in the art to provide a knee sleeve having an adjustable patella buttress which can be selectively configured and positioned for use on either right or left knees, thus eliminating the need for separate production and stocking of handed units.

SUMMARY OF THE INVENTION

The present invention overcomes the problems outlined above and provides a knee-supporting sleeve comprising posterior, proximal anterior and distal anterior panels formed of respective differential stretch materials. These panels are interconnected to present an elongated, tubular body adapted to fit over the knee area, with the posterior panel engaging posterior portions of the lower thigh, knee and upper calf, the proximal anterior panel engaging portions of the lower thigh above the knee, and the distal anterior panel engaging the patella and anterior portions of the knee and portions of the upper shin below the knee. In contrast to prior designs, the materials making up the posterior and proximal anterior panels (which are in practice identical) have a greater longitudinal (i.e., along the longitudinal axis of the tubular body) and lateral (i.e., transverse to the longitudinal axis of the body) stretchability than the material making up the patella and knee-engaging distal anterior panel. It has been found that such differential stretchability provides optimum compression and support for weakened knee joints.

In preferred forms, the knee sleeves of the invention include stiffened medial and lateral panels interposed between side margins of the posterior panel and the anterior panels in order to engage and support medial and lateral portions of the knee area; these medial and lateral panels may conveniently be formed as integral extensions of the distal anterior panel. These medial and lateral panels may also be reinforced by sewn-in-place metallic spiral straps extending the majority of the length of the tubular body.

The sleeves of the invention are also preferably provided with a patella-receiving opening in the distal anterior panel, as well as a unique patella buttress assembly. In particular, an exterior compartment is carried on the distal anterior panel in order to house therein a flexible rubber-like buttress. The compartment and buttress are of generally U-shaped, upwardly opening configuration, and adjacent portions of the compartment-defining material are provided with complemental VELCRO (the well known hook and loop attachment material) facings. Thus, the compartment may be selectively opened and the buttress therein trimmed and shifted so as to assume a size and position giving a desirable "lateral J" buttress for either left or right knees. After such trimming and manipulation, the buttress compartment can be reclosed by pressing together the complemental VELCRO facings. Thus, a universal buttressed knee sleeve is provided which can be readily modified by the user for either the left or right knee.

BRIEF DESCRIPTION OF THE DRAWINGS

FIG. 1 is an elevational view of a knee sleeve in accordance with the invention applied to a knee and illustrating the use of external attachment straps and a generally U-shaped supplemental exterior support;

FIG. 2 is a view similar to that of FIG. 1 but illustrating the knee sleeve without the external supplemental support;

FIG. 3 is a view similar to that of FIGS. 1–2, but showing the upper and lower attachment straps in a loosened condition;

FIG. 4 is an elevational view of a preferred knee sleeve in accordance with the invention, showing the buttress-receiving compartment opened, with the internal buttress partially removed for trimming and adjustment purposes;

FIG. 5 is a sectional view taken along line 5—5 of FIG. 3 and illustrating the detail the construction of the sleeve as well as the position of the patella buttress therein;

FIG. 6 is an enlarged view illustrating the buttress compartment opened to allow access to the internal rubber-like buttress.

DETAILED DESCRIPTION OF THE INVENTION

Figure 7:
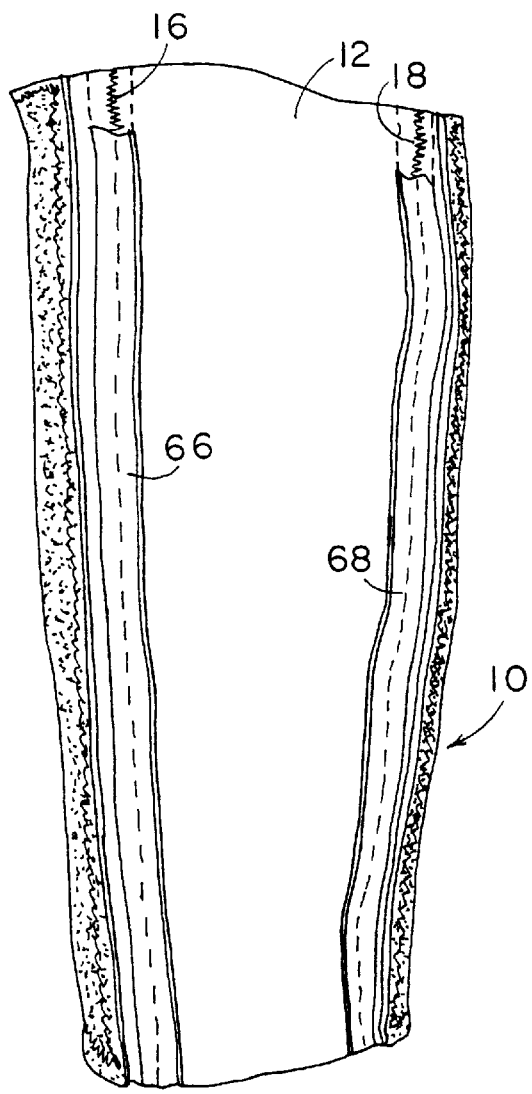
FIG. 7 is a rear elevational view of the preferred knee sleeve of the invention, depicting the anterior panel and seam lines.

Turning now to the drawings, and particularly FIGS. 4 and 7, a knee-supporting sleeve 10 is provided. The sleeve 10 is broadly made up of a posterior panel 12 and an anterior panel 14 sewn together along respective side seams 16, 18. The anterior panel 14 has two functionally different segments or panels, namely a proximal anterior panel 20 and a distal anterior panel 22. The panels 12 and 14 are interconnected as illustrated so as to define an elongated, tubular body 24 having a pair of opposed open ends and a continuous sidewall; as shown in FIGS. 1–3, the sleeve 10 is adapted to fit over the knee area, with posterior panel 12 engaging posterior portions of the lower thigh, knee and upper calf. The anterior panel 14 correspondingly engages and covers the anterior portions of the knee area; specifically, the proximal anterior panel 20 engages portions of the lower thigh above the knee, whereas the distal anterior panel 22 engages and supports the patella and anterior portions of the knee and portions of the upper shin below the knee. As best seen in FIGS. 1–3, the sleeve 10 is conventionally held in place by means of a pair of detachable VELCRO straps 26, 28 designed to wrap around the leg above and below the knee as shown.

In more detail, posterior panel 12 is preferably formed of a unitary segment of thin, lightweight, three-ply laminate material including an inner stretch of polyurethane film sandwiched between stretchable facing cloth made of 80% nylon and 20% spandex elastic material. This laminate is sold by Darlington Fabrics Corporation of New York under the designation DARLEXX®, and has a longitudinal elongation of about 110% and a lateral elongation of about 85%. The material has a moisture vapor transmission (breathability) of less than 4500 as measured by ASTM E96 and a hydrostatic resistance (waterproofness) of greater than 30 as measured by ASTM D751. The DARLEXX® product is described in U.S. Pat. No. 4,761,324, incorporated by reference herein.

The anterior panel 14 includes a segment 30 of the same DARLEXX® material as used for posterior panel 12. This segment 30 forms the innermost, skin-engaging portion of the entire anterior panel 14. The proximal anterior panel 20 is made up of the DARLEXX® laminate with only one modification. In particular, as best seen in FIG. 5, the upper margin of proximal anterior panel 20 is provided, on the inner surface thereof, with a silicone anti-slip band 32. This anti-slip band facilitates placement and holding of the sleeve 10 in place on the leg during walking or exercise. The band 32 is preferably formed by initially applying to the inner surface of panel 20 an uncured synthetic resin which directly adheres to the DARLEXX® material, and which is thereafter cured in place. In practice, the band 32 is formed of IPOCON adhesive commercialized by IPOS N.A., Inc. of Niagara Falls, N.Y. This adhesive is a silicone-based synthetic resin material described as polydimethylsiloxane interlaced with fillers and acetoxysilan. This adhesive has been found to properly adhere to the inner surface of the panel 20 and will not delaminate or erode during normal use. The band 32 is applied by brush application of the viscous IPOCON adhesive followed by a cure time of at least 24 hours, and most preferably about 72 hours. It is important that the anti-slip material be applied as a relatively thin layer, so as to not unduly limit the stretchability of the DARLEXX® material. Adequate stretchability is important in order to prevent a blood flow-restricting "tourniquet effect." Normally, the band 32 should have a thickness of from about 0.005–0.1 inches, and most preferably from about 0.01–0.05 inches.

The distal anterior panel 22 is made up of the innermost DARLEXX® material as described, as well as a segment 34 of 1/16 inch thickness of VELCRO-compatible UBL (unbroken loop) laminate neoprene which is stitched to the outer face of the segment 30 along stitch lines 31. The segment 34 includes a central panel section 36 which extends from the lower end of the sleeve 10 upwardly to the point where proximal anterior panel 20 begins. In addition, the segment 34 includes a pair of elongated antero-medial and antero-lateral panels 38, 40 which are likewise stitched to the underlying DARLEXX® segment 30 along axial stitch lines 41. The antero-medial and antero-lateral panel sections 38, 40 are provided with conventional reinforcing metallic straps therein which are captively retained by stitch lines 41 between the inner face of the panels 38, 40, and the adjacent outer face of the DARLEXX® segment 30.

The preferred neoprene laminate material used in forming the panels 22, 38 and 40 is commercially available and includes a central closed cell neoprene synthetic resin sheet faced on inner and outer surfaces by UBL VELCRO compatible nylon fabric. This material allows VELCRO attachment of straps or reinforcements, and also has been found to have complemental stretch characteristics relative to the DARLEXX® material.

Referring specifically to FIGS. 4–6, it will be observed that the distal anterior panel 22 is provided with a central patella opening 42 therethrough. A U-shaped, upwardly opening buttress-receiving compartment 44 is formed about opening 42 by appropriate stitching of the UBL neoprene laminate along arcuate stitch line 46 and respective vertical stitch lines 48, 50. An elongated, originally U-shaped, cylindrical silicone rubber buttress 52 is housed within the U-shaped compartment as shown. The periphery of opening 42 extending between the stitch lines 48, 50 is provided with an arcuate VELCRO strip 54 secured to the DARLEXX® material for mating the UBL neoprene laminate material making up the outer ply of panel 22. In this fashion, the buttress compartment can be selectively opened by separating strips 54 and the UBL material, thereby allowing access to buttress 52. In practice, the sleeve 10 is provided with an inner buttress 52 of U-shaped configuration as shown, which substantially fills the corresponding U-shaped compartment 44. The user initially opens the compartment as described, and appropriately trims the buttress 52 to remove a portion of one end thereof, thereby achieving an appropriate length for a "lateral J" buttress. The trimmed buttress 52 can then be shifted within the compartment so as to assume a proper "lateral J" position for either right or left knee wearing. The compartment is then closed by recompressing the UBL neoprene laminate and strip 54. It will thus be appreciated that with the present invention, only one style of sleeve need be manufactured and distributed; the user can readily manipulate the internal buttress 52 by trimming and shifting thereof, so as to give a proper "lateral J" buttress for either the right or left knee. This is a decided advantage in practice.

In order to affix the sleeve 10 in place, use is made of the straps 26 and 28 described above. These straps include a central VELCRO section 56 compatible with the UBL neoprene laminate, allowing the straps to be releasably secured to the outer faces of the panels 22, 38 and 40 as desired. The attachment straps 26, 28 are also provided with a simple buckle 58 allowing the free end of the strap to be threaded thereinto, with mating VELCRO sections 60 and 62 allowing the free end of the strap to be secured after passage through the buckle 58.

In order to provide still further support, a generally U-shaped stretchable neoprene support 64 may be applied to the distal anterior panel 22 adjacent opening 42 (see FIG. 1). To this end, the support 64 includes inner VELCRO strips at the bight and endmost regions thereof which are compatible with the UBL neoprene laminate making up the exterior portion panels 22, 38 and 40. Thus, the support 64 may be removably attached as shown to provide an additional degree of support.

The sewn seams 16, 18 are employed for securing together posterior panel 12 and DARLEXX® segment 30 forming the inner portion of anterior panel 14. These seam lines are formed by first conventionally stitching the marginal ends of the panel 12 and segment 30 together, followed by application of external facing of these seams with synthetic resin seam tapes 66, 68. This material is preferably an adhesive backed nylon jersey obtained from San Chemicals, Ltd. of Osaka, Japan and is designated Melco T-5000. This seaming material is adhesively heat-applied and firmly bonds to the DARLEXX in order to form a very secure final seam. Further information pertaining to this seaming material and methods of application thereof can be found in U.S. Pat. No. 5,382,223, incorporated by reference herein.

An important feature of the present invention reside in the fact that the material making up the posterior panel 12 and proximal anterior panel 20 have a greater longitudinal and lateral stretchability than the composite material making up the distal anterior panel 22. It has been found that such a combination of materials provides optimum variable stretch coefficients for maximum compression and knee joint conformity, allowing the user the greatest degree of mobility coupled with protective support. Moreover, these materials give highly advantageous thermal properties allowing evaporation of perspiration through areas of the knee joint where the greatest amount of heat is generated during exercise. This keeps the limb cooler when it is hot, and warmer when it is cold. The composite materials making up distal panels 22, 38 and 40 give great strength and durability at high stress areas of the knee joint. This is particularly the case with the use of an internal buttress support forming a part of the distal anterior panel 22.

I claim:

1. A knee-supporting sleeve comprising:

a posterior panel formed of a first material;

a proximal anterior panel formed of a second material; and a distal anterior panel formed of a third material, said posterior, proximal anterior and distal anterior panels being interconnected to present an elongated, tubular body adapted to fit over the knee area, with said posterior panel adapted to engage the posterior portions of the lower thigh, knee and upper calf, said proximal anterior panel adapted to engage the portions of the lower thigh above the knee, and said distal anterior panel adapted to engage the patella and anterior portions of the knee and the portions of the upper shin below the knee, said first and second materials having greater stretchability than said third material, said distal anterior panel presenting a patella-receiving opening therethrough with said material surrounding said opening, there being a patella-supporting buttress carried by said distal anterior panel and disposed at least partially about said opening.

2. The sleeve of claim 1, including an elongated medial and lateral panels interposed between the side margins of said posterior panel and said anterior panels, said medial and lateral panels adapted to respectively engage the medial and lateral portions of said knee area.

3. The sleeve of claim 2, said medial and lateral panels extending substantially the full length of said body.

4. The sleeve of claim 2, said medial and lateral panels including an elongated reinforcing strap therein.

5. The sleeve of claim 1, including structure defining a patella-receiving opening in said distal anterior panel.

6. The sleeve of claim 5, including a patella-supporting buttress carried by said distal anterior panel and located adjacent the periphery of said opening.

7. The sleeve of claim 6, said buttress being selectively shiftable for locating the member at a desired location relative to said opening.

8. The sleeve of claim 6, including compartment-defining structure on said distal anterior panel for receiving said buttress therein, said compartment-defining structure being selectively openable for allowing access to said buttress therein in order to allow trimming and/or shifting of the buttress.

9. The sleeve of claim 1, said panels being interconnected by a pair of elongated sewn seams adjacent the side margins of said posterior panel.

10. The sleeve of claim 1, said first and second materials being identical.

11. The sleeve of claim 10, said first and second material being a laminate comprising a synthetic resin film faced with stretchable nylon/spandex elastic material.

12. The sleeve of claim 1, said third material comprising said first material having fabric faced neoprene laminate stitched thereto.

13. The sleeve of claim 12, said fabric comprising a hook and loop attachment material compatible material.

14. The sleeve of claim 12, said third material comprising:

an inner layer of said first material; and an outer layer of UBL laminate neoprene stitched thereto, said UBL laminate being hook and loop attachment material-compatible.

15. The sleeve of claim 1, said posterior panel extending substantially the full length of said sleeve.

16. A knee-supporting sleeve comprising:

an elongated, tubular body presenting a sidewall having inner and outer surfaces and a patella-receiving opening therethrough;

a compartment on the outer surface of said sidewall of said body adjacent said opening; and an elongated knee buttress received within said compartment and shiftable therein, said compartment being openable for allowing access to said buttress therein in order to allow shifting, trimming and/or adjustment of said buttress relative to said compartment, whereby said buttress can be selectively shifted, trimmed and positioned as a right or left patella buttress.

17. The sleeve of claim 16, said compartment and buttress being generally U-shaped.

18. The sleeve of claim 16, said compartment comprising a segment of material secured to the outer surface of said body adjacent said opening with the compartment defined between the segment and body, adjacent portions of said body and segment proximal said opening being provided with complemental hook and loop attachment material permitting selective access to said compartment and said buttress therein.

19. The sleeve of claim 16, said buttress comprising a resilient cylindrical body.

20. A knee-supporting sleeve comprising:

a posterior panel formed of a first material;

a proximal anterior panel formed of a second material; and a distal anterior panel formed of a third material, said posterior, proximal anterior and distal anterior panels being interconnected to present an elongated, tubular body adapted to fit over the knee area, with said posterior panel adapted to engage the posterior portions of the lower thigh, knee and upper calf, said proximal anterior panel adapted to engage the portions of the lower thigh above the knee, and said distal anterior panel adapted to engage the patella and anterior portions of the knee and the portions of the upper shin below the knee, said first and second materials having greater stretchability than said third material, said distal anterior panel presenting a patella-receiving opening therethrough with said third material surrounding said opening, said posterior panel and said proximal anterior panel each having a stretchability throughout the respective lengths thereof which is greater than the stretchability of said distal anterior panel.

\* \* \* \* \*